United States Patent [19]

Zsadon et al.

[11] Patent Number: 5,204,355
[45] Date of Patent: Apr. 20, 1993

[54] 15-NITRO-2β, 3β-DIHYDRO- AND 15-NITRO-2β,3β,6,7-TETRAHYDROTABERSONINE DERIVATIVES, PHARMACEUTICAL COMPOSITIONS CONTAINING THEM AND PROCESS FOR PREPARING SAME

[75] Inventors: Béla Zsadon; Margit Barta née Bukovecz; Mária Szilasi; Tibor Keve; János Galambos; Viktória Bolya née Kassay; Sándor Szabó; Emília Répási, née Balogh; László Szporny; Béla Kiss; Egon Kárpáti; Éva Pálosi; Zsolt Szombathelyi; Ádám Sarkadi; Erzsébet Lapis; Anikó Gere; Mihály Bodó; Katalin Csomor; Judit Laszy; Zsolt Szentirmay, all of Budapest, Hungary

[73] Assignee: Richter Gedeon Vegyeszeti Gyar RT., Budapest, Hungary

[21] Appl. No.: 806,975

[22] Filed: Dec. 12, 1991

[30] Foreign Application Priority Data

Dec. 18, 1990 [HU] Hungary ............... 8313/90

[51] Int. Cl.$^5$ ............... C07D 471/16; A61K 31/475
[52] U.S. Cl. ........................ 514/283; 546/51
[58] Field of Search ............... 514/283; 546/51

[56] References Cited

U.S. PATENT DOCUMENTS 4,152,519 5/1979 Parcor ............... 546/51
4,888,351 12/1989 Imaki ............... 549/49

OTHER PUBLICATIONS

Lewin, Heterocycles 14, 1915 (1980).
Chem. Abstracts, vol. 94,157125H (1981) G. Lewin et al.

Journal of Chem. Society, Perkin Transactions 1. 1987, Letchworth, GB pp. 155 to 161.

*Primary Examiner*—Mark L. Berch
*Attorney, Agent, or Firm*—Herbert Dubno; Jonathan Myers

[57] ABSTRACT

The invention relates to novel 15-nitro-2β,3β-dihydro- and 15-nitro-2β,3β,6,7-tetrahydrotabersonine derivatives of the formula (I),

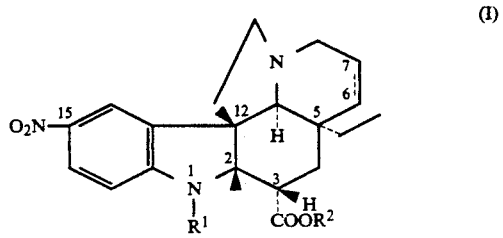

wherein
$R^1$ stands for hydrogen;
$R^2$ stands for hydrogen or a $C_{1-6}$alkyl group; and the symbol
= represents a single or double bond as well as their salts.

The invention further relates to pharmaceutical compositions containing the above compounds as well as a process for the preparation of the above compounds of formula (I) and of the pharmaceutical compositions.

The compounds of formula (I) exert a reducing or inhibitory effect on cerebral edema and show antihypoxic properties. Thus, they are useful for the prevention or treatment of brain injuries of various origin induced by hypoxia of the brain.

8 Claims, No Drawings

15-NITRO-2β, 3β-DIHYDRO- AND 15-NITRO-2β,3β,6,7-TETRAHYDROTABERSONINE DERIVATIVES, PHARMACEUTICAL COMPOSITIONS CONTAINING THEM AND PROCESS FOR PREPARING SAME

The invention relates to novel 15-nitro-2β, 3β-dihydro-and 15-nitro-2β, 3β, 6, 7-tetrah (according to the Chemical Abstracts' nomenclature 15-nitro-(2α, 5α, 12β, 19α)-aspidospermidine-3α-carboxylic acid derivatives) of the formula (I),

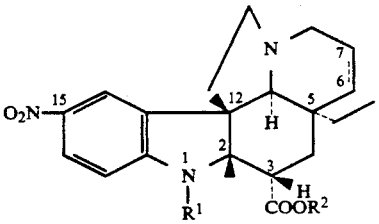

wherein
$R^1$ stands for hydrogen;
$R^2$ stands for hydrogen or a $C_{1-6}$ alkyl group; and the symbol
=== represents a single or double bond as well as their salts and cerebral edema-inhibiting pharmaceutical compositions containing these compounds as active ingredients. The invention also relates to a process for the preparation of these compounds and pharmaceutical compositions as well as to a method of treatment. The method of treating comprises administering a therapeutically effective dose or doses of the compound of the formula (I) or a pharmaceutically acceptable salt thereof or a pharmaceutical composition containing the same into the organism of a mammal including man for reducing or inhibiting cerebral edema.

The compounds of formula (I) may possess either basic or acidic character; accordingly their salts formed either with acids or bases are within the scope of the invention.

The compounds of formula (I) are novel compounds never published in the literature up to the present. All these compounds can be considered to be the derivatives of tabersonine a compoud the formula (II),

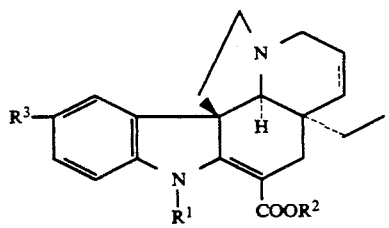

wherein $R^1$ and $R^3$ stand for hydrogen, $R^2$ stands for methyl and === represents a double bond, a known alkaloid of native origin. Their skeleton and the absolute configuration of their asymmetry centers in 5-, 12- and 19-positions are in agreement with those of the optically active, native (−)-tabersonine (chemically, according to the Chemical Abstracts nomenclature methyl 2,3,6,7-tetrahydro-(5α, 12β, 19α)-aspidospermidine-3-carboxylate).

According to another aspect of the invention, there is provided a process for the preparation of formula (I) and their salts, which starts from tabersonine or from its 6,7-dihydro derivative, i.e. (−)-vincadifformine, a known indole alkaloid.

Tabersonine, first isolated by Janot et al. (Bull. Soc. Chim. Fr. 1954, 707) is the main alkaloid of several plant species (such as Amnosia tabernaemontana, Voacanga africana, Rhazya orientalis and the like) belonging to the family of the Apocynaceae. Tabersonine can be obtained in large amounts from these raw materials by using simple methods and can be widely employed for partial systheses. The crystalline, highly pure tabersonine base prepared by known processes [Acta Chim. Acad. Sci. Hung. 67, 71 (1971); and Hungarian patent specification No. 196,404]and salts formed therefrom as well as optically active (−)-vincadifformine of high purity obtained by the catalytic hydrogenation of the $C_6$–$C_7$ double bond of tabersonine are particularly useful for the above purpose.

According to the process of the invention the compounds of formula (I) are prepared by
a) nitrating a tabersonine derivative of formula (II), wherein $R^1$ and the symbol === are as defined above, $R^2$ stands for a $C_{1-6}$alkyl group and $R^3$ stands for hydrogen, then
selectively reducing the $C_2$–$C_3$ double bond of the tabersonine derivative of formula (II) obtained as the main product, wherein $R^1$, $R^2$ and the symbol === are as defined above and $R^3$ represents a nitro group; or
b) nitrating an 1-acyltabersonine derivative of the formula (III),

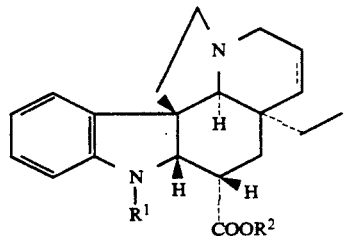

wherein $R^1$ means an acyl group and $R^2$ as well as the symbol === are as defined for formula (I), then
deacylating the 1-acyltabersonine derivative of formula (I) obtained wherein $R^1$ means an acyl group and $R^2$ as well as the symbol === are as defined for formula (I), and finally, if desired, saponifying or transesterifying the ester derivatives of formula (I) obtained, wherein $R^1$ and the symbol === are as defined for formula (I) and $R^2$ stands for a $C_{1-6}$alkyl group and/or, if desired, esterifying or converting to salts with bases or acids the compounds of formula (I) obtained, wherein $R^2$ means hydrogen and $R^1$ as well as the symbol; === are as defined for formula (I).

For preparing ester analogs which are different from the methyl ester, tabersonine or 6,7-dihydrotabersonine, respectively, is subjected to transesterification in an anhydrous alcohol corresponding to the ester desired, in the presence of a basic catalyst, e.g. sodium alkoxide, under heating. Alternatively, in the case of 6,7-dihydro derivatives, an analogous ester derivative of tabersonine may catalytically be transformed to the corresponding analogous ester derivative of 6,7-dihydrotabersonine.

The first step of the process a) is nitration. The nitration of tabersonine, 6,7-dihydrotabersonine and analogous 2,3-didehydro-(5α,12β,19α)-aspidospermidine-3-carboxylic acid derivatives is suitably carried anhydrous organic solvent by using a moderate excess of concentrated nitric acid. In this case the nitration leads to the 15-nitro derivative as main product.

The nitration of 6,7-dihydrotabersonine in trifluoroacetic acid to give 15-nitro-6,7-dihydrotabersonine was reported in: Heterocycles, 14, 1915 (1980); whereas the nitro derivatives of tabersonine and its ester analogs as well as the nitro derivatives of 6,7-dihydrotabersonine and its ester analogs have not been published up to the present.

After nitration the $C_2$–$C_3$ double bond of the thus obtained compounds of formula (II) is saturated by selective reduction. In order to achieve the selectivity, a reduction with zinc in a sulfuric acid - methanol medium had previously been suggested in the cases of tabersonine and some of its derivatives unsubstituted in the aromatic ring (Tetrahedron Letters, 1962, 235 and 271). In this case the yield was rather moderate and the stereochemistry of the thus formed $C_2$–$C_3$ saturated bond was uncertain. Later sodium cyanoborohydride (NaCNBH3) was used for this purpose [Tetrahedron, 35, 957 (1979); J. Chem. Soc. Perkin Trans. I. 1987, 155]. The literary references and also our own investigations have shown that the 2β,3β-dihydro structure was unambiguously formed by using this latter reducing agent. According to our best knowledge, no data have been reported up to now in the literature for the selective reduction of 2,3-didehydro-(5α,12β,19α)-aspidospermidine-3-carboxylic acid derivatives substituted by a nitro group on their aromatic ring.

The starting substances of the process b) according to the invention are 1-acyl-(2β, 5α, 12β, 19α)-aspido-spermidine-3α-carboxylic acid derivatives of formula (III). The compounds of formula (III) may be prepared from tabersonine or 6,7-dihydrotabersonine as starting substances. In the first step the $C_2$–$C_3$ double bond is saturated by a selective reduction carried out with sodium cyanoborohydride or by using zinc in a medium containing concentrated hydrochloric acid and methanol. Subsequently, the nitrogen atom in 1-position is acylated, preferably acetylated to give the starting compounds of formula (III). By using the sodium cyanoborohydride reduction the sequence of the above steps may be changed, i.e. the first step consists of an acylation and the second step involves reduction in a solution of glacial acetic acid.

The acylation, preferably acetylation may be carried out by means of methods known oer se. Preferred acetylating agents are acetic acid anhydride or acetyl chloride.

The starting compounds of formula (III) may be nitrated by employing methods commonly used, known from the literature. Suitably concentrated nitrio aoid is used in an anhydrous organic solvent. According to the literary reference J. Chem. Soc. Perkin Trans. I. 1987, 155 1-acetyl-2β,3β-dihydrotabersonine was nitrated with concentrated nitric acid in a trifluoroacetic acid medium to obtain 1-acetyl-15-nitro-2β,3β-dihydrotabersonine.

The acyl group bound to the nitrogen in 1-position may be removed by deacylation in the presence of a suitable catalyst. This desacylating reaction is preferably carried out in a $C_{1-6}$ alkanol in the presence of an alkaline metal alkoxide. Conveniently, the acylated product is dissolved in the alcohol corresponding to the ester and after addition of a catalytic amount of the corresponding sodium alkoxide the solution is permitted to stand.

If desired, the compound of formula (I) obtained by the above processes may be transformed into other products being within the scope of the formula (I) by using known methods. Thus, if desired, the ester derivatives of the formulaI (I), wherein $R^1$ and the symbol === are as defined for formula (I) and $R^2$ means a $C_{1-6}$ alkyl group, are saponified or transesterified and/or, if desired, the compounds of formula (I), wherein $R^2$ is hydrogen and $R^1$ and === are as defined for formula (I), are esterified and/or converted to salts with bases or acids.

In the specification with the term $C_{1-6}$alkyl group a straight or branched chain alkyl is meant, such as e.g. methyl, ethyl, n-propyl, isopropyl, n-butyl, isobutyl, secondary or tertiary butyl group as well as various straight and branched chain pentyl or hexyl groups.

Both organic and inorganic acids and bases may be used for the salt formation. Preferably such representatives of these are employed which do not induce any harmful effect in the doses to be administered. Preferred acids are e.g. acetic acid, citric acid, hydrochloric acid and phosphoric acid; advantageous bases are e.g.: the hydroxides of alkaline metals, such as sodium or potassium hydroxide; alkaline eart metal hydroxides, e.g. calcium or magnesium hydroxide; as well as organic nitrogen bases, e.g. tris(hydroxymethyl)amine or ammonia.

The inhibitory effect on the cerebral edema of the compounds of formula (I) was studied by using the method of P. Linnee et al. "L'oedéme cérébral induit chez le rat par le triéthylétain. Intérêt et limites comme méthode d'étude de antioedémateux cérébraux", Ann. Pharmaceutiques francaises, 42, 431 (1984)) as described hereinafter in detail.

Inbred male Hannover Wistar rats weighing 180 to 200 g were used in these examinations. Before starting and during the treatment the animals were kept on normal laboratory diet and received tap water ad libitum.

The cerebral edema was induced by the daily administration of 2.5 mg/kg of triethyl-tin chloride (abbreviated hereinafter as TET) for 5 days. TET (Merck-Schuchardt, Darmstadt, Germany) was dissolved in distilled water under stirring and the stirring was continued during the treatment, too. TET was orally administered to the animals every day at 7 o'clock a.m.

Both the reference drugs and test compounds were homogenized in a 0.5 % carboxymethylcellulose solution by using an Ultra Turrax mixer and stirring was continued also during the administration. The first dose of the reference and test compounds, respectively, was orally 5 given following the TET treatment by 1 or 6 hours, respectively. The administration was always carried out in a volume of 0.5 ml/100 g of body-weight. Each group consisted of 7 animals; the control group received only the solvent of TET (distilled water) and the vehicle used for the compounds (0.5% carboxymethylcellulose solution) in an identical volume and at the same time as described above.

The animals were decapitated on the 5th day of the treatment at 2 hours after the last treatment (with the test compound). The whole brain was rapidly removed, washed with cold 0.9 % saline, the moisture was removed by a filter paper, the brains were placed on aluminum foils previously weighed and the wet weights of the brains (together with the aluminum foil of known weight) were determined with an accuracy of one tenth mg on an electric balance (Precisa 80/A, PAG Oerlikon AG, Zurich, Switzerland).

Subsequently the brains were dried at 90° C. for 92 hours, then the gross dry weight (dry weight of the brain together with the weight of the aluminum foil) was again measured. With the knowledge of the dry and wet weights, the brain water content, i.e. the effect of treatment by the compound was calculated and expressed in the percentage of the protective effect by using the following formula:

$$\text{protective effect \%} = \frac{(TET - Ko) - (TET - V)}{(TET - Ko) - (Veh - Ko)} \times 100$$

wherein
(TET-Ko) means the percentage of average brain water content of the animals treated with TET and vehicle;
(TET-V) means the percentage of average brain water content of the animals treated with TET and the compound; and
(Veh-Ko) means the percentage of average brain water content of the animals treated with distilled water and vehicle.

The deviations of changes in the brain water content (and dry weight) were analyzed by the means of Student's "t" trial. The protective effect was considered to be significant when the brain water content was significantly altered on effect of the treatment.

The results of our measurements are summarized in Table 1.

TABLE 1

Effect of the test compound as well as vincamine, piracetam, idebenone and hydergine (used as reference drugs) on the TET-induced increase in the brain water content of rats

| Treatment | Dose μmol/kg | Brain water content % ± S.E.M. | Protective effect % |
|---|---|---|---|
| Experiment 1 | | | |
| Distilled water + vehicle | — | 78.16 ± 0.08 | — |
| TET + vehicle | — | 80.07 ± 0.11$^a$ | — |
| TET + 1704369 | 100 | 78.09 ± 0.09*** | 103.6 |
| TET + vincamine | 100 | 78.83 ± 0.15*** | 64.9 |
| Experiment 2 | | | |
| Distilled water + vehicle | — | 78.14 ± 0.11 | — |
| TET + vehicle | — | 79.54 ± 0.05$^a$ | — |
| TET + 1704369 | 100 | 78.15 ± 0.05*** | 99.3 |
| TET + vincamine | 100 | 78.70 ± 0.13*** | 59.6 |
| Experiment 3 | | | |
| Distilled water + vehicle | — | 78.32 ± 0.09 | — |
| TET + vehicle | — | 79.98 ± 0.14$^a$ | — |
| TET + 1708009 | 50 | 79.44 ± 0.11* | 32.5 |
| TET + idebenone | 100 | 79.75 ± 0.14$^{ns}$ | 14.0 |
| Experiment 4 | | | |
| Distilled water + vehicle | — | 78.38 ± 0.16 | — |
| TET + vehicle | — | 79.74 ± 0.21$^a$ | — |
| TET + 1704369 | 50 | 78.30 | 105.9 |
| TET + 1704594 | 50 | 78.61 | 82.9 |
| TET + vincamine | 50 | 79.31 | 31.6 |
| Experiment 5 | | | |
| Distilled water + vehicle | — | 78.48 ± 0.16 | — |
| TET + vehicle | — | 80.35 ± 0.21$^a$ | — |
| TET + piracetam | 100 | 80.04 ± 0.28$^{ns}$ | 6.7 |
| Experiment 6 | | | |
| Distilled water + vehicle | — | 77.76 ± 0.20 | — |
| TET + vehicle | — | 80.73 ± 0.27$^a$ | — |
| TET + hydergine | 30[1] | 79.97 ± 0.38$^{ns}$ | 25.6 |

TABLE 1-continued

Effect of the test compound as well as vincamine, piracetam, idebenone and hydergine (used as reference drugs) on the TET-induced increase in the brain water content of rats

| Treatment | Dose μmol/kg | Brain water content % ± S.E.M. | Protective effect % |
|---|---|---|---|
| TET + idebenone | 100 | 80.22 ± 0.16$^{ns}$ | 16.9 |

In the above Table 1 the vehicle is carboxymethylcellulose solution.

The chemical names of the compounds labelled by code numbers are as follows:
1704369: methyl 15-nitro-(2β, 5α, 12β, 19α)-aspidospermidine-3α-carboxylate
1708009: ethyl 15-nitro-(2β, 5α, 12β, 19α)-aspidospermidine-3α-carboxylate
1703594: methyl-15-nitro-6,7-didehydro-(2β, 5α, 12β, 19α)-aspidospermidine-(15-nitro-2β, 3β-dihydrotabersonine).

REFERENCE DRUGS USED

Piracetam: 2-oxo-1-pyrrolidineacetic acid amide;
Hydergine: (5'α, 10α)-9, 10-dihydro-12'-hydroxy- 2'-methylethyl)-5'-benzylergotamine-3+, 6', 18-trione monomethanesulfonate;
Idebenone: 5,6-dimethoxy-2-(10-hydroxydecyl)-3-methyl-p-benzoquinone;
Vincamine: (+) −14β-hydroxy-14α- methoxycarbonyl-14, 15- -dihydroeburnamenine.

ABBREVIATIONS a: significant difference from the group treated with distilled water and vehicle: $p < 001$;
*: significant difference from the group treated with TET + vehicle: $p < 0.05$;
***: significant difference from the group treated with TET + vehicle: $p < 0.001$;
ns: the difference is statistically not significant;
1 hydergine was used in a dose of 30 mg/kg in the above experiment.

The values shown in the above table are results of experiments carried out in various times. It is obvious that the method is well reproducible since the brain water content or the TET-induced enhancement of the brain water content, respectively, were constant in all of the experiments. Similarly, the reproducibility of the effects of compounds can also clearly be seen.

It is evident from the data of Table 1 that from the group of the compounds according to the invention a 100 % protection against the edema-inducing effect of TET was provided by the substance No. 1704369 administered in a dose of 100 μmol/kg and this effect could well be reproduced within the ranges of the biological variability. Another member of the group of the compounds, the substance No. 1708009 proved to be similarly effective and resulted in a 32.5 % protection even in the lower dose used.

By contrast piracetam, hydergine and idebenone used for the treatment of disturbances of various origin of the cognitive functions, did not produce any practically useful protective action under the experimental conditions described above. The compound No. 1704369 was even more effective than the structurally similar vincamine used also for the above indications (the latter drug produced a protective effect of 59 to 65 % when administered in the same dose).

The data obtained can be interpreted as follows.

The administration of triethyltin for a longer period induces a severe edema in the central nervous system of the experimental animals. Although both the white and the grey substance of the brain are effected, the increase of water content of the white substance (myelin) is more pronounced.

The mechanism of the toxicity of TET (including its effect inducing an increase in the brain water content) has not completely been cleared up till now. However, it is known that significant injuries are induced in the metabolic activity of the brain by TET (the cell respiration, the oxidative phosphorylation, the combustion of glutamate, succinate and glucose, and in a higher concentration also the combustion of pyruvate are damaged). As a consequence of the deterioration of the energy-producing processes (the intactness of which is essentially important for maintaining the integrity of brain cells), the sodium ion content of the brain is significantly elevated and the catecholamine and serotonine pools are partially depleted [Pharmacological Review 37, 365 (1985)]. Finally, the cellular injuries lead to severe functional deficiencies (e.g. motion disturbances, intense laesions of the learning and memory processes).

A part of the above changes can similarly be observed after cerebral ischaemia or hypoxia, respectively [J. Cerebral Blood Flow and Metabolism 1, 155 (1981)]and contribute in a high degree to the development of hypoxiaischaemia-induced cellular injuries (cell death) and functional injuries (cognitive functions).

The effect of the compounds according to the invention on the TET-induced edema is significant. Based on the experimental data illustrated above it can be expected that these compounds will be useful for the protection from or treatment of the cerebral hypoxia-ischaemia-induced primary injuries (e.g. edema) of various origin and their sequels (e.g. dementia).

The antianoxic action of the target compounds was studied by using the following test method.

ANTIHYPOXIC EFFECT ON MICE

Male mice (CFLP LATI) weighing 24 to 26 g were used in these experiments. The test compounds were orally administered in a volume of 10 ml/kg one hour before starting the experiment.

The animals were orally treated with various doses of the test compounds after starving for 16 hours. One hour following the treatment the animals were placed in air-tight glass cylinders of 100 ml volume and the survival time of the animals was measured. Each group consisted of 10 animals. Animals, surviving longer by 30 % than the average survival time of the control group treated with placebo, were considered to be protected. The ED50 value (the dose effective in 50 % of the animals) was calculated from the percentage of surviving animals by using probit analysis.

The results obtained are shown in Table 2.

TABLE 2

| Code No. of the active compound | Asphyxial anoxia ED$_{50}$ p.o. mg/kg |
|---|---|
| 1703594 | 56.3 |
| 1704369 | 49.4 |
| 1708009 | 62.0 |

TABLE 2-continued

| Code No. of the active compound | Asphyxial anoxia ED$_{50}$ p.o. mg/kg |
|---|---|
| 1700374 | >100.0+ |

+ineffective in a dose of 100 mg/kg

The compound of code No. 1700374 is 15-nitro-6,7-dihydrotabersonine, a known compound.

It is obvious from the results that in contrary to the 2,3-dihydro derivatives according to the invention, the known 6,7-dihydro derivative did not provide any protection against the cerebral hypoxia occurring as a consequence of edema or other pathological processes.

The compounds of formula (I) are used alone or in the form of their salts, suitably in formulations commonly I0 used in the therapy. These formulations may be solid, liquid or semiliquid and can be prepared by using filling, diluting, stability-enhancing, pH value- and osmotic pressure-influencing, flavouring and odourizing agents as well as formulation-promoting additives and auxiliaries commonly used for the preparation of such compositions.

The solid pharmaoeutical compositions may be e.g. dragées, capsules, cachets or powder ampoule compositions for the preparation of injection compositions. The liquid compositions are e.g. injectable or infusion preparations, elixirs, lotions and drops. Ointments, balsams, creams, shaking mixtures and suppositories are semiliquid compositions.

The pharmaceutical composition is administered to the patient in an amount containing the dose of the active ingredient needed to ensure the desired effect. This dose depends on the severity of the disease, on the body-weight and sensitivity to the active ingredient of the patient, the route of administration and the number of the daily treatments. Knowing the patient, a physician skilled in the art can safely determine the dose to be administered in a given case.

For simple administration the pharmaceutical compositions conveniently are prepared in the form of dosage units containing a single dose of the active ingredient or a low multiple or a half, third or fourth part thereof. Such dosage units are e.g. tablets which may be provided with a groove (or more grooves) facilitating to administer the half or fourth part of the tablet. The tablets may be coated with an enteric coat being insoluble in an acidic medium in order to ensure the release of the active ingredient content after leaving the stomach. A similar effect can be achieved by encapsulating the active ingredient.

The pharmaceutical compositions according to the invention usually contain 1 to 100 mg of active ingredient/dosage unit. Of course, the amount of the active ingredient may be higher or lower as defined in some compositions.

The invention is illustrated in more detail by the aid of the following non-limiting Examples.

EXAMPLE 1

Methyl 15-nitro-(2β, 5α, 12β, 19α)-aspidospermidine--3α-carboxylate (15=nitro-2β, 3β, 6,7 -tetrahydrotabersonine)

The solution of 50.7 g (150 mmole) of crystalline 6,7-dihydrotabersonine base in 250 ml of glacial acetic acid and 250 ml of acetonitrile is cooled to -5° C. and a mixture containing 20 ml of fuming nitric acid, 100 ml of glacial acetic acid and 100 ml of acetonitrile is dropped to the above solution at the same temperature during 10 minute while stirring, then stirring is continued for 15 minutes. After pouring the reaction mixture onto ice and diluting with water, it is made alkaline by adding ammonium hydroxide and the alkaloid bases liberated are extracted into methylene chloride. After evaporating the methylene chloride solution 57 g of a crude mixture of products are obtained.

This crude product is separated by chromatography on a column charged with 1 kg of silica gel. The main fraction obtained as the evaporation residue of the eluate (eluated with a mixture containing 90 % by volume of benzene and 1 % by volume of ethanol) is chromatographically pure 15-nitro-6,7-dihydrotabersonine. The yield is 33 g (85.7 mmole, 57 %), $[\alpha]D^{20}$- 747° (c=0.2, ethanol). UV spectrum ($\lambda$max): 207, 267 and 293 nm.

33 g (85.7 mmole) of the above 15-nitro-6,7-dihydrotabersonine are dissolved in 400 ml of glacial acetic acid and reduced by adding a total of 20 g of sodium cyanoborohydride in little portions at room temperature during 90 minutes while stirring. After stirring for an additional hour the reaction mixture is poured onto ice, diluted with water and alkalinized by adding ammonium hydroxide. The free alkaloid bases are extracted into methylene chloride. The organic solution is evaporated to give 31.5 g of a mixture of alkaloids which is subjected to chromatography in a column charged with 800 g of silica gel. After eluating with a mixture containing 99 % by volume of benzene and 1 % by volume of ethanol, the main fraction is evaporated to yield 21.5 g (55.6 mmole, 64.8 %) chromatographically pure title compound, m.p.: 175° C. (after recrystallization from ethanol), $[\alpha]D^{20}$= +69° (c=0.5, chloroform).

EXAMPLE 2

Methyl-15-nitro-(2$\beta$, 5$\alpha$, 12$\beta$, 19$\alpha$)-aspidospermidine-3$\alpha$- -carboxylate The solution of 5.04 g (15 mmole) of crystalline tabersonine in a mixture of 200 ml of anhydrous methanol and 80 ml of concentrated hydrochloric acid is reduced by 40 g of activated zinc while boiling under reflux until the selective reduction of the $C_2$-$C_3$-double bond completely proceeds. After decanting the solution is diluted with water, made alkaline and the free alkaloid base is extracted into benzene. After drying the benzene solution is clarified by flowing through a silica gel column and then evaporated to dryness to obtain 4.67 g (13.8 mmole, 92%) of 2$\beta$, 3$\beta$-dihydrotabersonine [methyl 6,7-didehydro-(2$\beta$, 5$\alpha$, 12$\beta$, 19$\alpha$)-aspidospermidine-3$\alpha$- -carboxylate according to the Chemical Abstracts nomenclature], which is recrystallized from ethanol, m.p. 64 -65° C., $[\alpha]D^{20}$= +5.5° (c=1.5, ethanol).

To a solution containing 3.38 g (10 mmole) of 2$\beta$, 3$\beta$-dihydrotabersonine in 25 ml of methylene chloride 10 ml of acetyl chloride are added and the reaction mixture is let to stand at room temperature for 10 hours (during this time the acetylation is going on). Thereafter, the reaction mixture is poured onto ice, the aqueous phase is neutralized by adding alkali, and the free alkaloid base is extracted into methylene chloride. Evaporation of the methylene chloride solution gives 3.6 g (9.5 mmole, 95%) of 1- acetyl-2$\beta$, 3$\beta$- dihydrotabersonine [methyl 1-acetyl-6,7-didehydro-(2$\beta$, 5$\alpha$, 12$\beta$, 19$\alpha$) -aspidospermidine-3$\alpha$-carboxylate according to the Chemical Abstracts' nomenclature], which melts at 139°-140° C. after recrystallization from ethanol, $[\alpha]D^{20}$ = +59° (c=0.5, ethanol).

3.04 g (8 mmole) of 1- acetyle-2$\beta$, 3$\beta$-dihydrotabersonine dissolved in ethanol are hydrogenated by using palladium/carbon catalyst. After evaporation 3.05 g (8 mmole, 100%) of 1- acetyl-2$\beta$,3$\beta$, 6,7-tetrahydrotabersonine [methyl 1--acetyl-(2$\beta$, 5$\alpha$,12$\beta$,19$\alpha$)-aspidospermidine-3$\alpha$-carboxylate according to the Chemical Abstracts' nomenclature] are obtained, which melts at 136°-138° C. after recrystallization from ethanol, $[\alpha]D^{20}$ = +89° (c=0.5, ethanol).

3.17 g (7.5 mmole) of 1-acetyl-2$\beta$, 3$\beta$, 6,7-tetrahydrotabersonine dissolved in 25 ml of trifluoroacetic acid are nitrated with 0.7 ml of 96% nitric acid. After pouring onto ice the reaction mixture is neutralized by ammonium hydroxide and the alkaloid base liberated is extracted into benzene. The solution is clarified by flowing it through Brockmann II alumina layer and then evaporated to dryness to obtain 2.86 g (6.7 mmole, 89%) of methyl-1- -acetyl-15-nitro-(2$\beta$, 5$\alpha$, 12$\beta$, 19$\alpha$)-aspidospermidine-3$\alpha$-carboxylate (1-acetyl-15-nitro)-2$\beta$, 3$\beta$, 6,7-tetrahydrotabersonine) as an amorphous evaporation residue, $[\alpha]D^{20}$= +33° (c=0.5, ethanol). UV spectrum ($\lambda$max): 206, 233 and 317 nm.

A catalytic amount of sodium methoxide is added to a solution containing 2.14 g (5 mmole) of methyl-1-acetyl--15-nitro-(2$\beta$, 5$\alpha$, 12$\beta$, 19$\alpha$) aspidospermidine-3$\alpha$-carboxylate) in 40 ml of anhydrous methanol, then the mixture is let to stand at room temperature for 24 hours to achieve the deacetylation. After evaporating the methanolic solution the residue is diluted with water and extracted with benzene. The benzene solution is clarified by flowing it through Brockmann II alumina layer and then evaporated to dryness to yield 1.77 g (4.6 mmole, 92%) of methyl 15--nitro-(2$\beta$, 5$\alpha$, 12$\beta$, 19$\alpha$)-aspidospermidine-3$\alpha$-carboxylate (15-nitro-2$\beta$3$\beta$,6,7-tetrahydrotabersonine) as evaporation residue which, after recrystallization from ethanol, proved to be identical in all respects with the crystalline product prepared in Example 1, m.p.: 175° C., $[\alpha]D^{20}$= +69° (c=0.5, chloroform). This product did not give melting point depression after mixing it with the product prepared according to Example 1.

EXAMPLE 3

Methyl 15-nitro-(2$\alpha$, 5$\alpha$, 12$\beta$, 19$\alpha$)-aspidospermidine-3$\alpha$--carbxylate hydrochloride (15=nitro-2$\beta$, 3$\beta$, 6,7-tetrahydrotabersonine hydrochloride)

After dissolving g of methyl 15-nitro--(2$\beta$, 6$\alpha$, 12$\beta$, 19$\alpha$)-aspidospermidine-3$\alpha$-carboxylate base in 20 ml of ethanol under gentle heating, 30 ml of aqueous hydrochloric acid solution of 1 mole/litre concentration are added and after cooling the mixture is permitted to stand. The crystalline hydrochloride precipitates from the solution to give a yield of 0,80 g, m.p.: 103° C. The UV absorption maxima of this hydrochloride are identical to those of the alkaloid base.

EXAMPLE 4

Ethyl 15-nitro=(2$\beta$, 5$\alpha$, 12$\beta$, 19$\alpha$)-aspidospermidine-3$\alpha$--carboxylate After dissolving 6.72 g (20 mmole) of crystalline tabersonine base in 300 ml of anhydrous ethanol containing 0.5 g of sodium ethoxide, the solution is boiled under gentle reflux for 6 hours while continuously distilling out the methanol liberated from the transesterifying reaction. After evaporation of the reaction mixture ethyl 2,3,6,7-tetradehydro-(5$\alpha$, 12$\beta$, 19$\alpha$)-aspidospermidine-3-carboxylate (the ethyl ester homolog of tabersonine) is obtained, $[\alpha]D^{20}= -390°$ (c=0.2, ethanol), the crystalline hydrochloride of which melts at 124–126° C.

The above product is hydrogenated in ethanolic solution by using palladium-carbon catalyst for saturating the $C_6$–$C_7$ double bond. The saturation completely proceeds in a selective manner to give amorphous (oily) ethyl 2,3-didehydro-(5α, 12β, 19α)-aspidospermidine-3-carboxylate (i.e. the ethyl ester homolog of 6,7-dihydrotabersonine), $[\alpha]D^{20}= -535°$ (c=0.2, ethanol). The crystalline hydrochloride of this product melts at 137–140°C.

3.89 g (10 mmol) of crystalline ethyl 2,3-didehydro--(5α, 12β, 19α)-aspidospermidine-3-carboxylate are nitrated as described in Example 1 to obtain 2.18 g (5.5 mmole, 55%) of ethyl 15-nitro-2,3-didehydro--(5α, 12β, 19α)-aspidospermidine-3-carboxylate, -1008° (c=0.2, chloroform). UV spectrum (λmax): 208, 263 and 289 nm.

2.18 g (5.5 mmole) of ethyl 15-nitro-2,3-didehydro--(5α, 12β, 19α)-aspidospermidine-3-carboxylate are selectively reduced by using sodium cyanoborohydride (NaCNBH3) as described in Example 1 to obtain 1.34 g (3.35 mmole, 61 %/) of the named produce which, after recrystallization from ethanol, melts a 182–183° C., $[\alpha]D^{20}= -69.5°$ (c=0.3, chloroform) UV spectrum (λmax): 209, 238, 263 and 322 nm.

EXAMPEL 5

Butyl 15-nitro-(2β, 5α, 12β,19α)-aspidospermidine-3α-carboxylate 6.72 g (20 mmole) of crystalline tabersonine are transesterified in anhydrous butanolic solution containing a catalytic amount of sodium butoxide as described in Example 4. After evaporating the reaction mixture butyl 2,3,6,7-tetradehydro-(5α, 12β, 19α)-aspidospermidine-3--carboxylate (the butyl ester homolog of tabersonine) is obtained as an oily evaporation residue, $[\alpha]D^{20}= -322°$ (c=0.2, chloroform).

Subsequently, the $C_6$–$C_7$ double bond of the above compound is saturated by catalytic hydrogenation as described in Examle 4 to give butyl 2,3-didehydro--(5α, 12β, 19α)-aspidospermidine-3-carboxylate, $[\alpha]D^{20}= -476°$ (c=0.2, chloroform), the crystalline hydrochloride of which melts at 135–137° C.

After nitrating 4.16 g (10 mmole) of crystalline butyl 2,3-didehydro-(5α, 12β, 19α)-aspidospermidine-3--carboxylate hydrochloride as described in Example 1, the $C_2$–$C_3$ double bond is seleotively reduced to obtain 1.41 g (3.3 mmole, 33%) of the final product butyl 15-nitro--(2β, 5α, 12β, 19α)-aspidospermidine-3α-carboxylate as evaporation residue. UV spectrum (λmax): 209, 238, 263 and 322 nm.

EXAMPLE 6

Methyl 15-nitro-6,7=didehydro-(2β, 12β, 12β, 19α)--aspidospermidine-3α-carboxylate (15-nitro-2β, 3β-dihydrotabersonine)

A solution containing 7.45 g (20 mmole) of crystalline tabersonine hydrochloride in a mixture of glacial acetic acid and acetonitrile is nitrated with fuming nitric acid as described in Example 1. The main product of the nitration is chromatographically pure methyl 15-nitro-2,3,6,7-tetrahydro-(5α, 12β, 19α)-aspidospermidine-3-carboxylate (15-nitrotabersonine) obtained as evaporatopm residue in a yield of 4.04 g (10.6 mmole, 53%), $[\alpha]D^{20}= -467°$ (c=0.2, ethanol). UV spectrum (λmax): 207, 266, 292 and 397 nm. After recrystallization from methanol the product melts at 152–153 ° C.

The thus obtained 15-nitrotabersonine is selectively reduced by using sodium cynoborohydride in glacial acetic acid solution as described in Example 1 to give 2.70 g (7 0 mmole, 66%) of chromatographically pure methyl 15-nitro-6,7-didehydro-(2β, 5α, 12β, 19α)-aspidospermidine-3α-carboxylate as main product which, after recrystallization from ethanol, melts at 131° C, $[\alpha]D^{20}= -58°$ (c=0.2, ethanol).

EXAMPLE 7

15-Nitro-=6,7-didehydro-(2β, 5α, 12β, 19α)--aspidospermidine-3o-carboxylic acid and sodium salt (15-nitro-2β, 3β-dihydrotabersoninic acid)

After adding 300 ml of concentrated hydrochloric acid and 200 g of activated zinc granulate to 33.6 g (100 mmole) of crystalline tabersonine base dissolved in 700 ml of anhydrous methanol the solution is boiled under reflux for 3 hours. After filtration the solution is evaporated, the residue is diluted with ice-water, made alkaline and the alkaloid bases liberated are extracted into methylene chloride. The dried methylene chloride solution is evaporated to dryness, the residue (containing a little amount of unchanged tabersonine beside 2β, 3β-didehydrotabersonine) is dissolved in 500 ml of 1 N ethanolic potassium hydroxide solution and saponified by boiling under reflux for 2 hours. By acidifying the solution with hydrochloric acid the carboxylic acids are liberated and the carboxylic acid formed from the unchanged tabersonine is decarboxylated by gentle boiling. After dilution the solution is again made alkaline and the decomposition product of tabersoninic acid, i.e. 1,2,6,7-tetradehydroaspidospermidine is extracted into benzene. After adjusting the pH value of the solution to 6, the free 6,7--didehydro-(2β, 5α, 12β, 19α)-aspidospermidine-3α-carboxylic acid is extracted into methylene chloride. Evaporation of the solution yields 22 g (78 mmole, 68 %) of 6,7--didehydro-(2β, 5α, 12β, 19α)-aspidospermidine-3α-carboxylic acid which, after recrystallization from acetone, melts at 160–162° C., $[\alpha]D^{20}= +14°$ (c=0.4, methanol). UV spectrum (λmax): 208, 250 and 307 nm.

6,48 g (20 mmole) of the above product are dissolved in 100 ml of anhydrous methylene chloride, 20 ml of acetyl chloride are added and the acetylation is continued at room temperature for 24 hours. After pouring onto ice the aqueous solution is adjusted to pH 6 by adding alkali and then is extracted with methylene chloride. After drying the organic phase is evaporated to give 6.72 g (18.4 mmole, 92 %) of 1-acetyl-6,7-didehydro-(2β, 5α, 12β, 19α)--aspidospermidine-3α-carboxylic acid as evaporation residue which, after recrystallization from ethanol, melts at 193–195° C., $[\alpha]D^{20}= +30°$ (c=0.4, methanol). UV spectrum (λmax): 209, 253 and 285 nm.

3.65 g (10 mmole) of the above acetylated derivative dissolved in 40 ml of trifluoroacetic acid are nitrated with 2 ml of 96% nitric acid for 20 minutes at room temperature while stirring. After pouring onto ice, the mixture is adjusted to a pH value of 6 by adding alkali and is extracted with methylene chloride. After drying the organic phase is evaporated and the residue is recrystallized from ethanol to give 3.08 g (7.5 mmole, 75 %) of 1-acetyl-15-nitro-6,7-didehydro-(2β, 5α12β, 19α)--aspidospermidine-3α-carboxylic acid, m.p.: 229–230° C,. $[\alpha]D^{20}= +79°$ (c=0.3, methanol). UV spectrum (λmax): 209, 235 and 341 nm.

For deacylation 1.64 g (4 mmole) of the above nitro derivative are dissolved in 50 ml of anhydrous ethanol and after adding 2 ml of 1% ethanolic sodium ethoxide solution the reaction mixture is maintained at room temperature overnight. After evaporation the residue is dissolved in 25 ml of water, the pH value is adjusted to 6 and the mixture is extracted with methylene chloride. After drying the solution is evaporated to obtain 1.25 g (3.4 mmole, 85 of 15-nitro-6,7-didehydro-($2\beta$, $5\alpha$, $12\beta$, $19\alpha$)-aspidospermidine-$3\alpha$-carboxylic acid, m.p. 231-234 crystallization from acetone, $[\alpha]D^{20}=-44°$ (c=0.2, methanol).

An aliquot portion of the acid thus obtained is dissolved in ethanol and after adding an equivalent amount of sodium ethoxide, the solution is evaporated to dryness to obtain the sodium salt in a yield of 100% in the form of a white powder. UV spectrum ($\lambda$max): 213, 238, 270 and 329 nm.

EXAMPLE 8

PREPARATION OF TABLETS

| Ingredients: | mg |
|---|---|
| a) Tablets weighing 150 mg and containing 5 mg of active ingredient each | |
| Active ingredient | 5 |
| Gelatine | 3 |
| Magnesium stearate | 2 |
| Talc | 5 |
| Potato starch | 40 |
| Lactose | 95 |
| b) Tablets weighing 300 mg and containing 50 mg of active ingredient each | |
| Active ingredient | 50 |
| Polyvidone | 6 |
| Magnesium stearate | 3 |
| Talc | 9 |
| Potato starch | 84 |
| Lactose | 148 |

The powder mixture of the composition defined above under a) or b), respectively, is pressed to tablets weighing 150 mg or 300 mg, respectively, each by wet granulation or compression in usual manner. Each of the tablets contains 5 or 50 mg, respectively, of the active 0 ingredient.

We claim:

1. A compound of the formula (I),

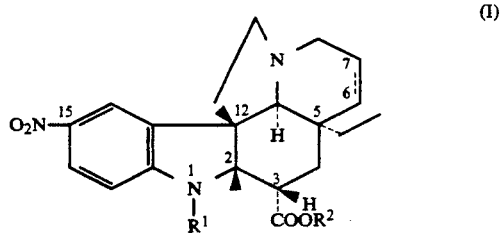

wherein
 $R^1$ stands for hydrogen;
 $R^2$ stands for hydrogen or a $C_{1-6}$alkyl group; and the symbol
 === represents a single or double bond or a salt thereof.

2. Methyl 15-nitro-($2\beta$, $5\alpha$, $12\beta$, $19\alpha$)--aspidospermidine-$3\alpha$-carboxylate or a salt thereof as defined in claim 1.

3. Ethyl 15-nitro- ($2\beta$, $5\alpha$, $12\beta$, $19\alpha$)--aspidospermidine-$3\alpha$-carboxylate or a salt thereof as defined in claim 1.

4. Butyl 15-nitro-($2\beta$, $5\alpha$, $12\beta$, $19\alpha$)--aspidospermidine-$3\alpha$- carboxylate or a salt thereof as defined in claim 1.

5. Methyl 15-nitro-6,7 -didehydro--($2\beta$, $5\alpha$, $12\beta$, $19\alpha$)-aspidospermidine-$3\alpha$-carbosylate or a salt thereof as defined in claim 1.

6. 15-Nitro-6,7-didehydro--($2\beta$, $5\alpha$, $12\beta$, $19\alpha$)-aspidospermidine-$3\alpha$-carboxylic acid or a salt thereof as defined in claim 1.

7. A pharmaceutical composition reducing or inhibiting the cerebral edema, which comprises as active ingredient a therapeutically effective amount of a compound as defined in claim 1 or a pharmaceutically acceptable salt thereof in admixture with additives or auxiliaries commonly used in pharmaceuticals.

8. Method for cerebral edema-reducing or -inhibiting treatment of a mammalian subject which comprises administering to the mammalian subject to be treated a therapeutically effective does of a compound as defined in claim 1 or a pharmaceutically acceptable salt thereof alone or in the form of a pharmaceutical composition.

* * * * *